US00PP14975P3

(12) United States Plant Patent
Whitcomb

(10) Patent No.: US PP14,975 P2
(45) Date of Patent: Jul. 6, 2004

(54) CRAPE MYRTLE PLANT NAMED 'WHIT VII'

(50) Latin Name: *Lagerstroemia indica*
Varietal Denomination: crape myrtle Whit VII

(75) Inventor: Carl Whitcomb, Stillwater, OK (US)

(73) Assignee: Lacebark, Inc., Stillwater, OK (US)

( * ) Notice: Subject to any disclaimer, the term of this patent is extended or adjusted under 35 U.S.C. 154(b) by 166 days.

(21) Appl. No.: 10/189,805

(22) Filed: Jul. 3, 2002

(65) Prior Publication Data

US 2004/0006803 P1 Jan. 8, 2004

(51) Int. Cl.[7] ..... A01H 5/00

(52) U.S. Cl. ..... Plt./252

(58) Field of Search ..... Plt./252

*Primary Examiner*—Kent Bell
(74) *Attorney, Agent, or Firm*—Streets & Steele; Jeffrey L. Streets; Frank J. Campigotto

(57) ABSTRACT

A new and distinct variety of crape myrtle, *Lagerstroemia indica*, which is characterized by a slow to moderate growth habit; leathery leaves which emerge crimson and quickly change to medium green; moderate seed set; inflorescences which are 8 to 16 inches tall and 6 to 10 inches wide; flower buds which are oxblood red; and flowers with tightly grouped and highly wrinkled petals. The new variety is also characterized by a long bloom period.

4 Drawing Sheets

Genus and species: *Lagerstroemia indica.*
Varietal denomination: crape myrtle WHIT VII.

BACKGROUND OF THE INVENTION

The present invention relates to a new and distinct variety or cultivar of the ornamental shrub, *Lagerstroemia indica*, commonly known as crape myrtle.

The crape myrtle shrub is native to eastern China and was introduced into North America in the late 1700's. Since then, this popular ornamental shrub has been grown extensively across the southern half of the continent. Over the years, seedlings of *Lagerstroemia indica* or hybrids between *L. indica* and *L. fauriei* have been selected for various growth forms, flower colors, or other features and propagated asexually. An assortment of methods has been utilized in attempting to develop improved varieties of crape myrtle and several have had U.S. Plant Patents issued.

For example, U.S. Plant Pat. No. 4,182, U.S. Plant Pat. No. 4,183, U.S. Plant Pat. No. 4,184, and U.S. Plant Pat. No. 4,185 disclose and claim a series of four new varieties of *Lagerstroemia indica* produced by crossing previously known varieties. Each of these varieties was characterized as having a weeping growth habit at maturity. U.S. Plant Pat. No. 5,302 also discloses a new variety of crape myrtle exhibiting a weeping growth habit at maturity.

U.S. Plant Pat. Nos. 6,365 and 6,383 discloses a variety of crape myrtle derived from seedlings treated with a mutation-inducing chemical. U.S. Plant Pat. Nos. 10,296, 10,297, 10,312, 10,319 and 11,342 also disclose new varieties of crape myrtle derived from seedlings where one or more of the parents were treated with a mutation-inducing chemical.

It is generally known that ethyl methane sulfonate (EMS), sodium azide, and colchicine are capable of producing plant mutations. Since one of the grandparents of the new variety of crape myrtle was treated with these compounds, the present invention may be such a mutant seedling.

SUMMARY OF THE INVENTION

The present invention involves the discovery of a new and distinct variety of crape myrtle, *Lagerstroemia indica*, which has been given the cultivar name 'Whit VII' and is characterized by a multi-branched, moderate growth rate large shrub that may reach a height of 6 to 12 feet at maturity. Leaves of the plant are more leathery than the species average and emerge crimson and quickly change to medium green. Inflorescences are panicles 8 to 16 inches tall and 6 to 10 inches wide. Flower buds and individual petals are oxblood red. Old flowers fall from the inflorescence cleanly and with little discoloration. Flowering generally begins in July in North Central Oklahoma and flowering continues until frost. Seed head production is moderate which further enhances the long flowering.

DETAILED BOTANICAL DESCRIPTION

Figure 1:
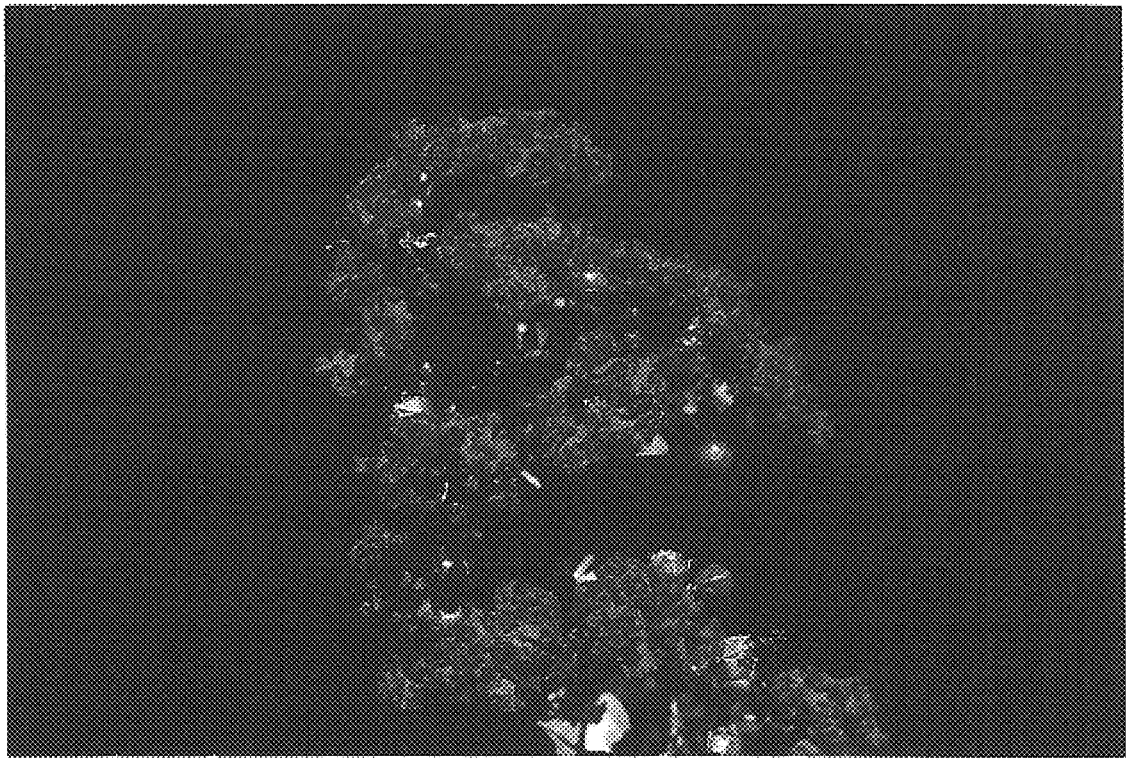
FIG. 1 is a photographic view in full color of the flowering of my new crape myrtle plant.

The new variety of crape myrtle, which has been given the cultivar name 'Whit VII', was selected from about 1600 seedlings grown from a $6^{th}$ generation original seedling plant from when this research began in 1986. The parent seedling was selected because of near red flowers, dark foliage, resistance to powdery mildew and that produced seeds with good germination and seedling vigor. Prior to planting, the seeds were treated with ethyl methane sulfonate (EMS), sodium azide and colchicine. EMS is generally known to be capable of producing plant mutations and colchicines is generally known to be capable of causing doubling or tripling of chromosomes. No attempt was made to control pollination: therefore the pollen could have come from any of the surrounding crape myrtle seedlings. Treated seeds were planted in flats in a greenhouse. After the seeds germinated, the seedlings were transplanted into small containers. Any seedlings that developed powdery mildew or had poor vigor were rouged out and the remainder were planted in rows in an open field for further evaluation. The new variety was selected from the population in the field for the unique flower color, resistance to powdery mildew and leathery foliage. It is probably a mutant seedling arising from the EMS, sodium azide and colchocine treatments. Mutant plants resulting from EMS treatments often have thicker than normal leaves, reduced seed production and may have an occasional flower with variegation among normally solid colored flowers. Such characteristics have been observed in this new variety of crape myrtle, although the flower variegation is slight and only occasionally expressed.

Softwood cuttings taken from the original WHIT VII plant have been successfully rooted in a medium of peat and perlite under intermittent mist. Subsequent cuttings taken from plants produced from the previous cuttings of the WHIT VII original plant have been similarly rooted. Growth, flowering, and flower and foliage color and disease resistance remain consistent with the WHIT VII. The plant does not reproduce from seed. Asexual reproduction of the new plant by cuttings taken in Stillwater, Okla., has shown that the unique features of this new crape myrtle are stable and reproduced true to type in successive generations.

A detailed description of the new variety of crape myrtle follows: Unless otherwise noted, the description is of a field plant, approximately three years old, grown in north central Oklahoma.

Parentage: Selected from about 1600 crape myrtle seedlings grown from a selected $6^{th}$ generation seedling parent. The seeds were treated with EMS sodium azide and colchicine to induce mutations. The male parent is not specifically known as pollination resulted from natural insect activity among hundreds of seedlings adjacent to the female plant. The thick leathery leaves, occasional flower with slight variegation, long bloom time and partial sterility are indications that the new variety may be a mutant seedling.

Growth: The plant is a slow to moderate grower with moderate branching and upright oval to rounded shrub growth habit. The initially discovered WHIT VII plant reached a height of 6 feet in 4 years in the field with minimum care. Vegetative growth is rapid for a brief period in the spring but slows before flowering and little vegetative growth occurs once flowering begins.

Figure 4:
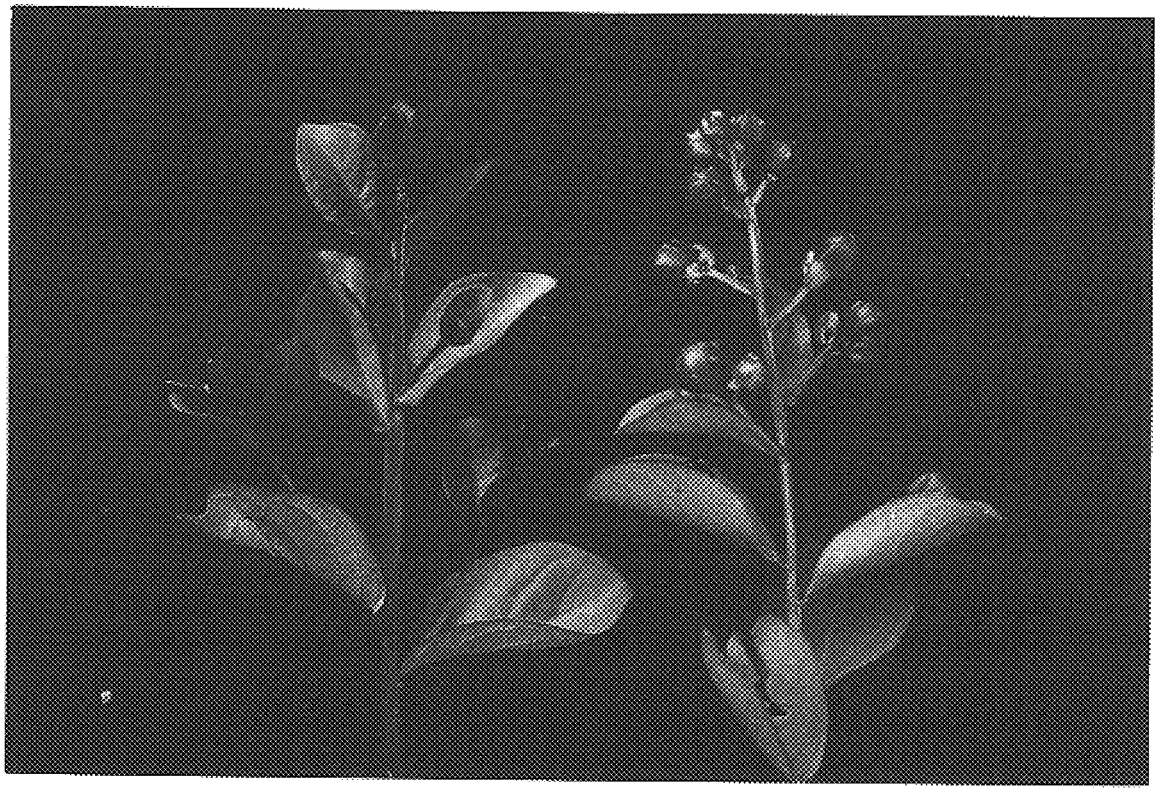
FIG. 4 is a photographic view in full color of the color transition of new leaves to mature leaves (left) and flower bud, pedicel and twig color in an early stage of flowering (right) on the plant in FIG. 1.

Branches: Current season's stems, exposed to direct light are crimson, greyed-purple group 187-A and CIE .410, .298, 3.4 (FIG. 4, left) (Color notation from The Royal Horticulture Colour Chart, 1966 and the Commission International de l'Eclairage, 1931). Current seasons stems that terminate in flower buds are at first green, then increase in crimson coloring (FIG. 4, right) becoming crimson, greyed-purple group 187-A and CIE .410, .298, 3.4 on sides exposed to full sun at time of flowering (FIG. 2) Under north central Oklahoma conditions, new growth ranges from 3 inches to 15 inches, having stem diameters from about 3/32 inch to about 9/32 inch.

Bark: Bark is typical of *L. indica* species and is exfoliating. One, two and three year old stems of WHIT VII range from grayed-orange group 177-B (CIE .407, .353, 16.1) to 17-D (CIE .402, .347, 26.9). Four or five year old stems range from gray-brown group 199-A (CIE .409, .402, 14.8) or 199-B (CIE .390, .387, 22.1) when shaded or grayed-green group 197-A (CIE .350, 364, 17.9 or 197-B (CIE .346, .360, 22.8) when exposed to sun.

Foliage: Leaves are similar in size to the species average, but are more thick and leathery and with good retention even under severe drought conditions. New leaves emerge crimson, grayed-purple group 185-A and CIE Coordinates.519, .312, 8.5 and quickly change to medium green (FIG. 2), Green group 137-A (R.H.S.) and CIE .325, .419, 10.0. Upper and lower leaf surfaces of new leaves are the same color. Leaf color varies with light intensity, nutrition, and growing conditions. Under leaf surfaces of mature leaves range from green group 138-A (CIE .325, .416, 16.5) to 138-B (CIE .334, .408, 25.6), except where a leaf is turned or folded so that a portion of the under leaf surface is exposed to sun. When exposed to sun, the under leaf surface remains 187-A (CIE .410, .289, 3.4) or 187-B (CIE .479, .296, 5.1). Foliage has been highly resistant to powdery mildew. Leaves range from one inch to 2.25 inches long and 0.5 to 2 inches wide. At the tip, the shape of the leaves are acute to obtuse. At the base, the leaves are obtuse to slightly acute. The leaves are sessile or nearly so as there is no defined petiole.

Figure 2:
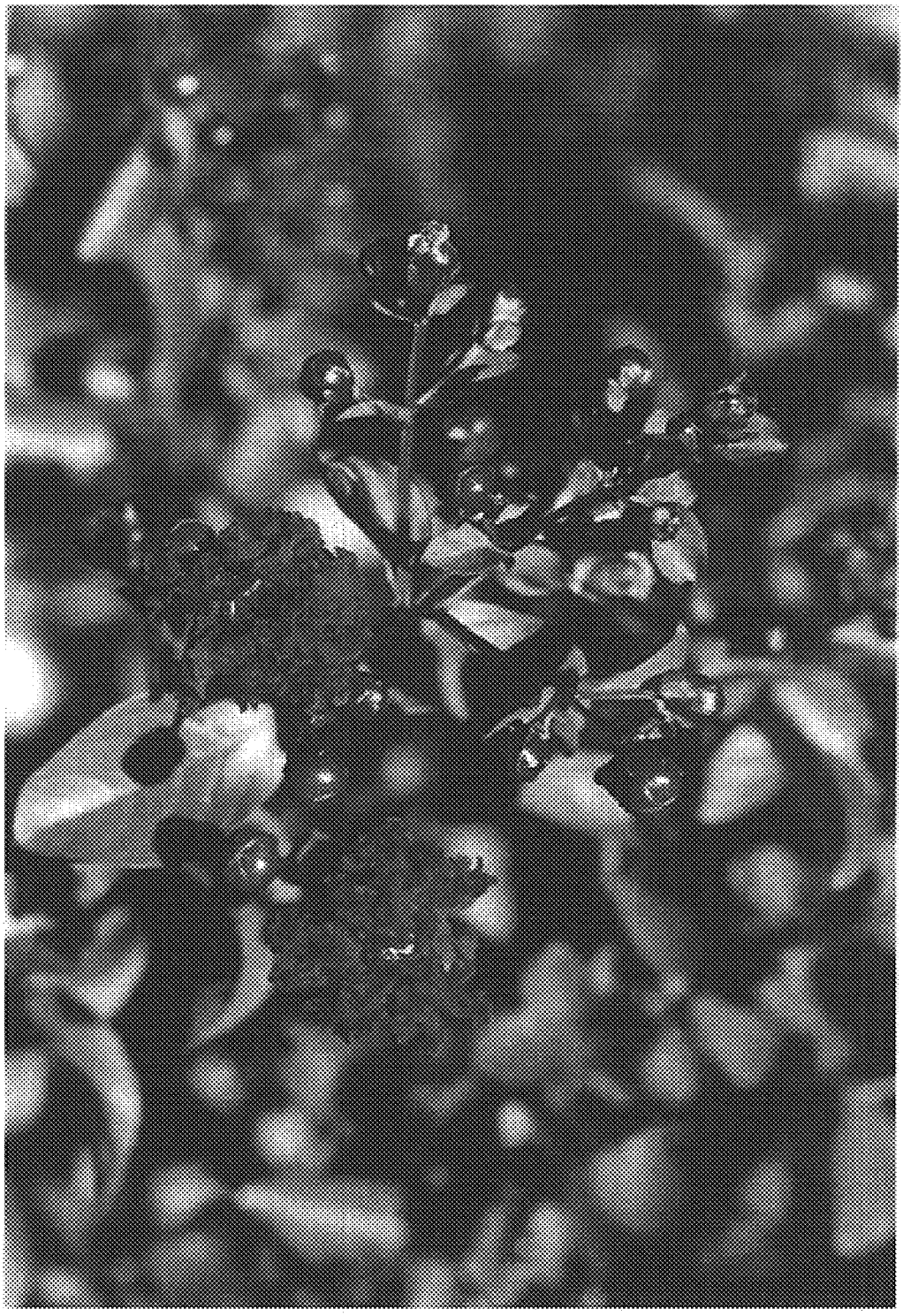
FIG. 2 is a photographic view in full color of an inflorescence panicle of the plant in FIG. 1 with flower buds, flowers, young stems, and mature foliage.
Figure 3:
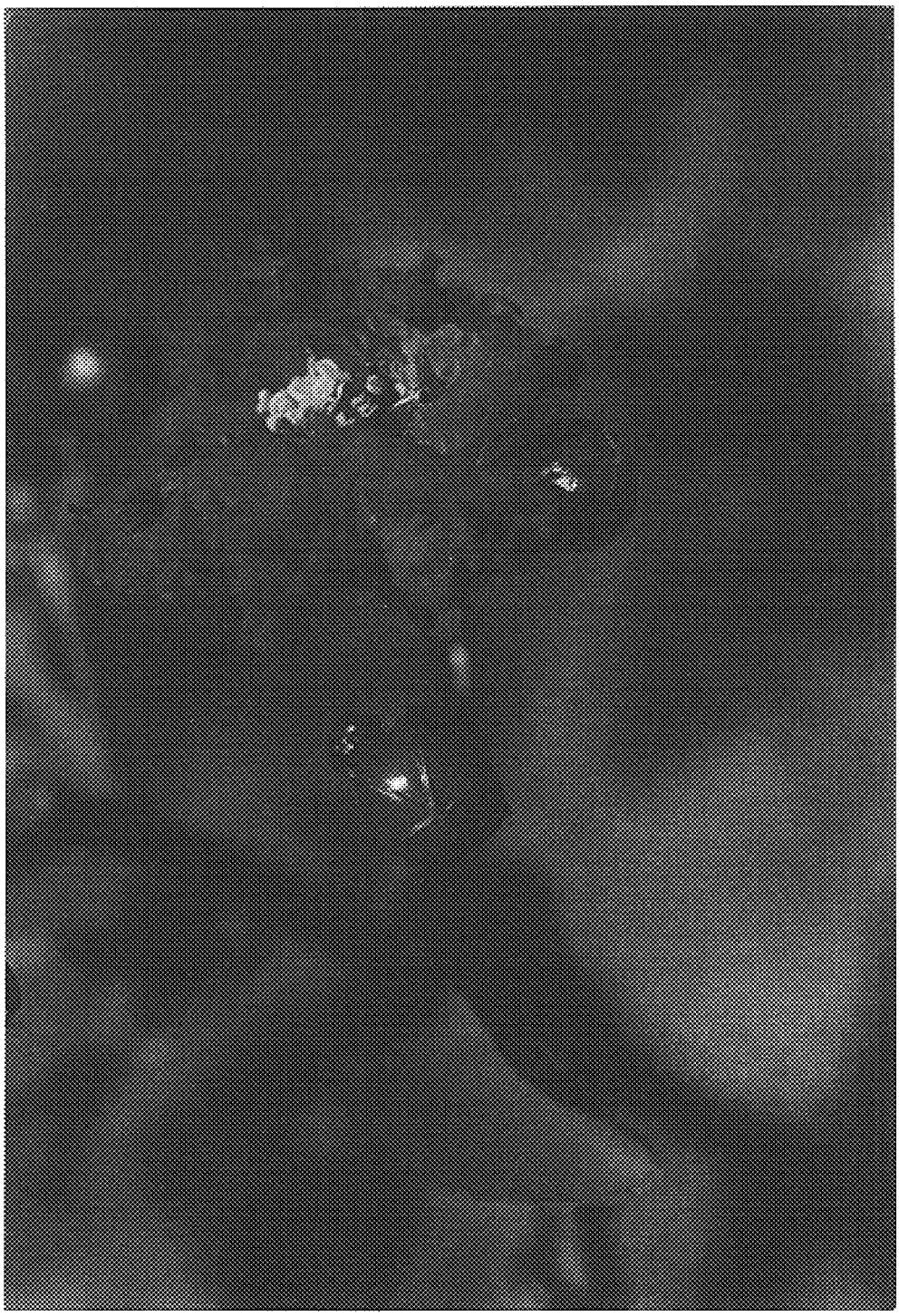
FIG. 3 is a photographic view of the plant in FIG. 1 in full color of flower buds and a flower showing the slight color variation that occasionally occurs.

Flowers: Both the upper and lower surfaces of individual flowers are oxblood red, greyed-purple group 183-A and CIE .467, .319, 6.9 or 183-B and CIE .457, .317, 8.2 (FIGS. 1,2,3). Blades of petals are more wrinkled and gathered than most crape myrtle flowers, completely or mostly covering the stamens. The presence of a slightly lighter petal (s) is only occasionally expressed (FIG. 3) and varies with temperature, light intensity, and growing conditions, but is generally absent. The flowers range from 0.75 to 1.75 inches in diameter and have no fragrance. Flowers typically have 6 petals, but occasionally have 5 or 7 petals. Petal sizes are highly variable within a flower and between flowers in terms of the extent of folds or wrinkles. As the flowers age, they generally fall cleanly from the inflorescence without discoloring or becoming unattractive. Unopened flower buds are oxblood red, greyed-purple group 183-A and CIE .467, .319, 6.9 to 183-C and CIE .460, .311, 9.7 (FIGS. 2 and 3). Flower buds are round, or nearly so, with six lines of dehiscence. Bud size increases with age, from just a bump to about 3/16 to 5/16 inch diameter at opening. Size of the flower buds vary with growing conditions. Inflorescences are panicles typically 8 to 16 inch long and 6 to 10 inches wide. The lastingness of an individual bloom is extremely variable depending on growing conditions. When growing conditions are moderate, with temperatures in the 80's to 90's and moisture is available, individual flowers remain attractive for 10–15 days. When water is limited and temperatures are high, flowers begin to lose their attractiveness after 4 to seven days. As with all panicle inflorescences, flowers begin to open at the base and progress to the tip. Larger panicles will retain attractive flowers longer than smaller panicles. Panicle size is greatly influenced by growing conditions.

The new variety begins flowering in July in North Central Oklahoma and continues into October. This period is longer than most seedlings and cultivars of crape myrtle known to me. Flowering typically continues during periods of drought and extreme heat. Seed set is moderate which contributes to the extended flowering. There are six sepals but when the flower opens, the wrinkled petals typically obscure the sepals. Each sepal is pie shaped as ⅙ of a sphere, with the size of the sepal depending on the size of the bud. Many flowers do not expose the anthers or pistils at all and the anthers and pistils vary greatly between flowers.

Cold hardiness: The new variety of crape myrtle has withstood temperatures of −2° F. with no injury. The top was killed to the soil line at −15° F. in February 1996, but quickly regrew the following spring and was four feet tall and flowering by mid- July. The top of the initially discovered WHIT VII as well as asexually propagated offspring were killed in October 2000 when, on October 3, the temperature was 92° F., then on October 9, dropped to 23° F. With the arrival of spring 2001, all plants produced vigorous growth and were flowering by early July. This was a distinct contrast to many other seedlings under evaluation that were killed entirely or were very slow to recover from the cold injury.

Comparison to U.S. Plant Pat. No. 10,296 and No. 11,342: In comparing the presently claimed variety ('Whit VII') to that claimed in U.S. Plant Pat. No. 10,296 ('Whit II') and No. 11,342 ('Whit IV') distinct differences can be noted. The 'Whit VII' variety has flowers that are darker red. The 'Whit VII' flowers are 183-A to 183-B (R.H.S.) whereas the 'Whit II' variety has flowers 46-A (R.H.S.) and the 'Whit IV' variety have flowers 45-A and 45-C (R.H.S.). Also, 'Whit VII' is a slow to moderate growing shrub that may only reach 6 to 12 feet at maturity, whereas 'Whit II' and 'Whit IV' grow much more vigorous and may reach a mature height of 20 feet or more.

I claim:

1. A new and distinct variety of crape myrtle plant, substantially as illustrated and described.

* * * * *